(12) United States Patent
Ibrahim et al.

(10) Patent No.: US 6,860,668 B2
(45) Date of Patent: Mar. 1, 2005

(54) METHOD AND APPARATUS FOR IMPROVED STIFFNESS IN THE LINKAGE ASSEMBLY OF A FLEXIBLE ARM

(75) Inventors: Tamer Ibrahim, Danville, CA (US); Steve Geyster, Milton, MA (US); James Gleeson, Columbus, OH (US); Thomas D. Haubert, Columbus, OH (US); James A. Prescott, Columbus, OH (US)

(73) Assignee: Endoscopic Technologies, Inc., Danville, CA (US)

( * ) Notice: Subject to any disclaimer, the term of this patent is extended or adjusted under 35 U.S.C. 154(b) by 0 days.

(21) Appl. No.: 10/268,397

(22) Filed: Oct. 9, 2002

(65) Prior Publication Data

US 2003/0165352 A1 Sep. 4, 2003

Related U.S. Application Data

(60) Provisional application No. 60/327,990, filed on Oct. 9, 2001.

(51) Int. Cl.$^7$ ............................................... F16C 11/06
(52) U.S. Cl. ............................. 403/56; 403/57; 403/90; 600/228; 600/229; 248/181.1
(58) Field of Search ................ 403/53, 55–58, 403/90, 122; 600/228, 229; 248/160, 181.1, 181.2, 288.31, 481

(56) References Cited

U.S. PATENT DOCUMENTS

| 4,949,927 | A |   | 8/1990 | Madocks et al. |
|---|---|---|---|---|
| 5,348,259 | A | * | 9/1994 | Blanco et al. ............ 248/276.1 |
| 5,624,381 | A | * | 4/1997 | Kieturakis .................. 600/206 |
| 5,727,569 | A |   | 3/1998 | Benetti et al. |
| 5,899,425 | A | * | 5/1999 | Corey Jr. et al. ........ 248/276.1 |
| 6,361,493 | B1 | * | 3/2002 | Spence et al. .............. 600/210 |

* cited by examiner

*Primary Examiner*—John R. Cottingham
*Assistant Examiner*—Michael P. Ferguson
(74) *Attorney, Agent, or Firm*—GSS Law Group; Gregory Scott Smith; Carol D. Titus (57) ABSTRACT

The invention includes linkage assemblies comprising coupled links with metallic contact surfaces with improved stiffness. The inventors found significant mechanical problems with all previous descriptions of metallic contact links sufficient to preclude their commercial use. These metallic contact links are a significant improvement over existing plastic ball and metal joint, or all plastic beads as found in the prior art. The invention includes methods providing these links and high friction couplings between them, as well as the linkage assemblies and flexible arms resulting from these processes.

79 Claims, 7 Drawing Sheets

METHOD AND APPARATUS FOR IMPROVED STIFFNESS IN THE LINKAGE ASSEMBLY OF A FLEXIBLE ARM

CROSS-REFERENCE TO PRIORITY APPLICATION DOCUMENTS

This application claims the benefit of provisional patent application Ser. No. 60/327,990 filed Oct. 9, 2001, the specification and drawings of which are hereby incorporated by reference in their entirety.

TECHNICAL FIELD

The present invention relates to articulating load bearing flexible arms, particularly suited for use as surgical tissue stabilizers, and more particularly to increasing the stiffness of such an articulating column when in the locked configuration.

BACKGROUND ART

Flexible arms or, as they are often called, articulable columns, have many uses. For example, they are often used for positioning tools, article supports, or for locking measuring apparatus. In surgery, it is common practice to mount them as adjustable supporting brackets on a side rail of an operating table to support retractors, endoscopes and other surgical devices.

U.S. Pat. No. 4,949,927 discloses an articulable column and, more particularly, describes prior art columns of the ball and socket type which are flexible in their normal state and which, by application of tension from a central cable, become rigid.

Recent developments in heart surgery require stronger and more rigid adjustable brackets. In particular, a procedure has been introduced for carrying out cardiac bypass surgery without stopping the patient's heart. In this procedure, a device called a "tissue stabilizer" is used.

A specific prior art example, U.S. Pat. No. 5,727,569 teaches that the tissue stabilizer is attached to the wall of the heart by drawing a vacuum in an array of suction cups. With one or more such devices attached to the wall of the heart, the site at which the repair is to take place can be held fixed while the heart continues to beat.

A tissue stabilizer is often supported using a lockable articulating column, such as disclosed in U.S. Pat. No. 5,348,259. A lockable articulating column is described as a flexible, articulable column having a central tensioning cable strung through a series of ball and socket members. Each socket member has a conical opening with internal teeth engagable with a ball made of an elastomeric polymer. When the cable is tensioned, the sockets move toward each other and the balls become indented by the teeth of the socket. The column becomes rigid when the central cable is tensioned. Releasing the tension returns the column to the flexible state.

Figure 1:
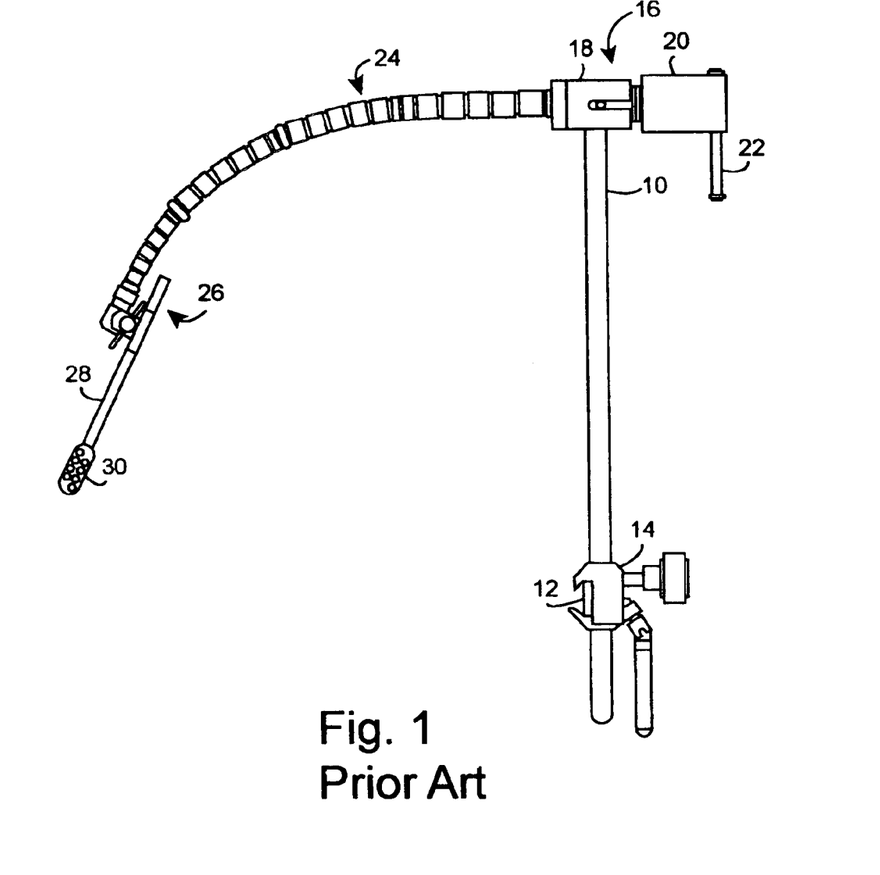
FIG. 1 is an elevational view illustrating a tissue stabilizer supported from the side rail of an operating table by a bracket as found in the prior art of U.S. Pat. No. 5,899,425.

FIG. 1 is an elevational view illustrating a tissue stabilizer supported from the side rail of an operating table by a bracket as found in the prior art of U.S. Pat. No. 5,899,425.

The assembly in FIG. 1 includes vertical post 10 attached to side-rail 12 of an operating table (not shown) by a clamp 14. The post 10 often has plural facets, which cooperate with the clamp to prevent rotation of the post relative to the clamp. A tension block 16, mounted at the top of post 10, comprises a mounting block 18 and a rotatable member 20.

In FIG. 1, one end of a flexible arm 24 is connected to the side of mounting block 18 opposite to the side having the rotatable member 20. Flexible arm 24 comprises a series of articulating elements connected to one another by ball-and-socket joints. The number of ball and socket members may be increased or decreased depending on the use of the articulating column. The flexible arm 24 has a clamp assembly 26 mounted at its other end. The clamp assembly 26 holds the shank 28 of tissue stabilizer 30.

Typically, tensioned mounting block 18 has an internal passage receiving a screw 32. Affixed to the screw is a transverse pin riding in slots formed in opposite sides of mounting block 18. The engagement of the pin with the slots prevents the screw from rotating relative to mounting block 18. The threads of the screw engage internal threads in a rotatable member 20, which also has an internal shoulder that can engage with the screw's head.

The tension cable is often a braided structure made of metal specifically built to withstand cyclical tensile fatigue. The cable may be pre-stretched to minimize further elongation of the cable caused by the application of tension. Turning the rotatable member 20 often supports cable tensions in the range of 5 to 1000 lbs.

Plastic links have a significant problem when used in a surgical theatre, they often cannot be reused due to difficulties in cleaning them. Metallic links, if feasible, would be easier to clean, reducing a costly form of surgical waste.

While there are references in the cited prior art to metal links in a flexible arm linkage assembly dating back to 1990, the inventors have only found plastic links actually in the market. The references in the cited prior art will be discussed in the next few paragraphs.

Prior art, plastic link components were found by the inventors to undergo deflections of up to a factor of 1000% for plastics such as polyethylene when tensioned. Metallic link components typically deflect by less than 50%. This difference in the materials turns out to require an entirely different approach to determining useful metallic links and their contact surfaces. The percentages used above were percent elongation derived from the reference: *Materials Science and Engineering*, 3rd Edition, W. Callister copyright 1985, which is hereby incorporated by reference.

U.S. Pat. No. 4,949,927 teaches in FIG. 6 and its associated discussion about a link integrating a ball and rod made of aluminum. The inventors found that this link was inoperable, due to a low coefficient of friction. By having the low coefficient of friction, such links slipped easily, far below the point of usefulness.

U.S. Pat. No. 5,899,425 teaches (FIG. 2, Col. 4, lines 7–11) "The flexible, articulating arm 24, as shown in FIG. 2, comprises a series of elements, preferably made of stainless steel . . . . Each element has a convex, spherical surface at one end and a concave, spherical surface at the other end."

In the Summary of U.S. Pat. No. 5,899,425 (Column 2, lines 35–57), "The bracket is characterized by an interference fit between the spherical balls and their sockets. The diameter of each ball is preferably . . . larger than the diameter of the socket into which it fits. The sockets are hemispherical or almost hemispherical, and their walls are sufficiently flexible to allow the balls to enter them The very small difference in diameter, and the flexibility of the socket walls, allows the balls and sockets to be engaged over an area of contact. The terms 'area of contact' and 'area contact,' . . . mean contact between a ball and a socket over a substantial area in a common sphere, greater than approximately 20% of the total surface area of the sphere, and is distinguishable from 'line contact,' which is contact between a ball and socket over a circular line or a narrow band having an area which is substantially less than 20% of the total area of the sphere corresponding to the larger of the ball or socket. The area of contact extends from the periphery of the socket to the envelope of the perimeter of the cable opening in the concave spherical surface and the circle defining the end of the convex spherical surface adjacent to the cable opening therein. The contact area is preferably approximately 30% to 40% of the total surface area of a corresponding sphere."

The inventors found that U.S. Pat. No. 5,899,425 was both contradictory and inoperable in its teaching regarding metallic link components. First, maximizing the stainless steel contact area actually reduces the frictional force needed for stiffness. The disclosure from the Summary was appropriate for a plastic link component, but failed to account for the physical characteristics of stainless steel as well as alloys of iron and titanium, which do not deflect anywhere near as much as plastics.

Unlike, the prior art plastic articulating columns that are highly textured and consequently need only low tensile loads for fair rigidity, metallic link contact surfaces behave differently. This is due to the inherently lower interface friction of semi-smooth metallic mating convex and concave surfaces. Friction forces are directly proportional to these distributed contact forces. While two mating spherical surfaces would produce a large contact area, the distributed contact forces are relatively low because they are widely dispersed.

There is an additional problem with highly textured metallic contact surfaces. They would be difficult to clean, posing a health risk if reused in a surgical setting.

Note that a link will also be known herein as a bead.

The inventors know of no disclosure or teaching which provides for an effective metallic link for use in the linkage assembly of a flexible arm. What is needed is such an effective metallic link.

In summary, there is a need for increased stiffness in articulating joints, particularly in flexible arm linkage assemblies. There is a need for reusable links within a surgery, leading to needing metallic, reusable links. And there is a need for reusable links providing increased stiffness in flexible arm linkage assemblies.

SUMMARY OF THE INVENTION

The invention address the needs discussed in the background. The invention increases the stiffness of flexible arm linkage assemblies, by increasing the friction between link contacts when in a locked configuration.

One embodiment of the invention includes a flexible arm linkage assembly provided with a tensioning cable. The linkage assembly includes a first link with a first contact surface composed of a first contact material, and a second link with a second contact surface composed of a second, differing contact material. A high friction coupling between the first link and the second link is created by the first contact surface contacting the second contact surface when induced by the tensioning cable.

Each of the contact materials is primarily composed of a respective metallic compound, providing a higher coefficient of friction between the two contacting surfaces than would result from both contacting surfaces being composed of the same contacting material. The contacting materials are primarily composed of metallic compounds.

A flexible arm including the invention provides an increased range of motion and better stabilization of surgical instruments.

The contacting metallic compounds are further preferred to be primarily composed of alloys including at least one of iron, copper and titanium. The contacting metallic compounds are still further preferred to be at least two of the following: stainless steel, titanium, and nitinol, which will refer herein to Ni—Ti alloys.

Metallic links have a significant advantage when used in a surgery, they can be sterilized and reused many times. Using metal linkage assemblies reduces the waste products and lowers the costs associated with the use of flexible arms.

The invention includes increasing the overall metallic link to metallic link friction as a result of optimized contact geometry between the links, based upon the metallic composition of the contacting link surfaces.

Another embodiment of the invention includes optimization of metallic bead to metallic bead contact friction comprising the following steps. Maximizing the coefficient of friction between the first contact material of the first contact surface and second contact material of the second contact surface by selecting the first and second contact materials. Determining a ball diameter and conical angle to maximize frictional forces in static equilibrium based upon the coefficient of friction.

The inventors found that determining the ball diameter and conical angle maximizing static frictional forces required optimizing away from maximized contact area for a number of metals, including alloys of at least titanium, and iron, and in particular, stainless steel.

Using stainless steel for both contact surfaces, the inventors experimentally proved that they had discovered the first practical metallic link for flexible arms, providing significant improvement in the mechanical stiffness of the joint over typical plastic link components. This new metallic link used the interface geometry that resulted from their new approach to interface geometry determination.

The inventors further experimentally proved that they could make an even better joint using contact materials of stainless steel and titanium for the respective contact surfaces based upon the optimized interface geometry. The joint formed from the stainless steel contacting titanium beads had greatly improved stiffness over anything the inventors know of.

The invention includes methods of providing linkage assemblies using metallic links, as well as the linkage assembly and flexible arm as products of these methods.

The invention provides a flexible arm, also known as an articulating column, with the strength to stabilize devices holding a beating or stopped heart for an incision or the operation of a scope.

DETAILED DESCRIPTION OF THE INVENTION

Various embodiments built in accord with the invention will be discussed. The invention increases the stiffness of flexible arm linkage assemblies, by increasing the friction between link contacts, when in a locked configuration operating similarly to existing plastic based linkage assemblies.

The invention includes a flexible arm linkage assembly provided with a tensioning cable. The linkage assembly includes a first link with a first contact surface composed of a first contact material, and a second link with a second contact surface composed of a second, differing contact material. A high friction coupling between the first link and the second link is created by the first contact surface contacting the second contact surface when induced by the tensioning cable.

Each of the contact materials is primarily composed of a respective metallic compound, or compounds, providing a higher coefficient of friction between the two contacting surfaces than would result from both contacting surfaces being composed of the same contacting material.

Figure 2:
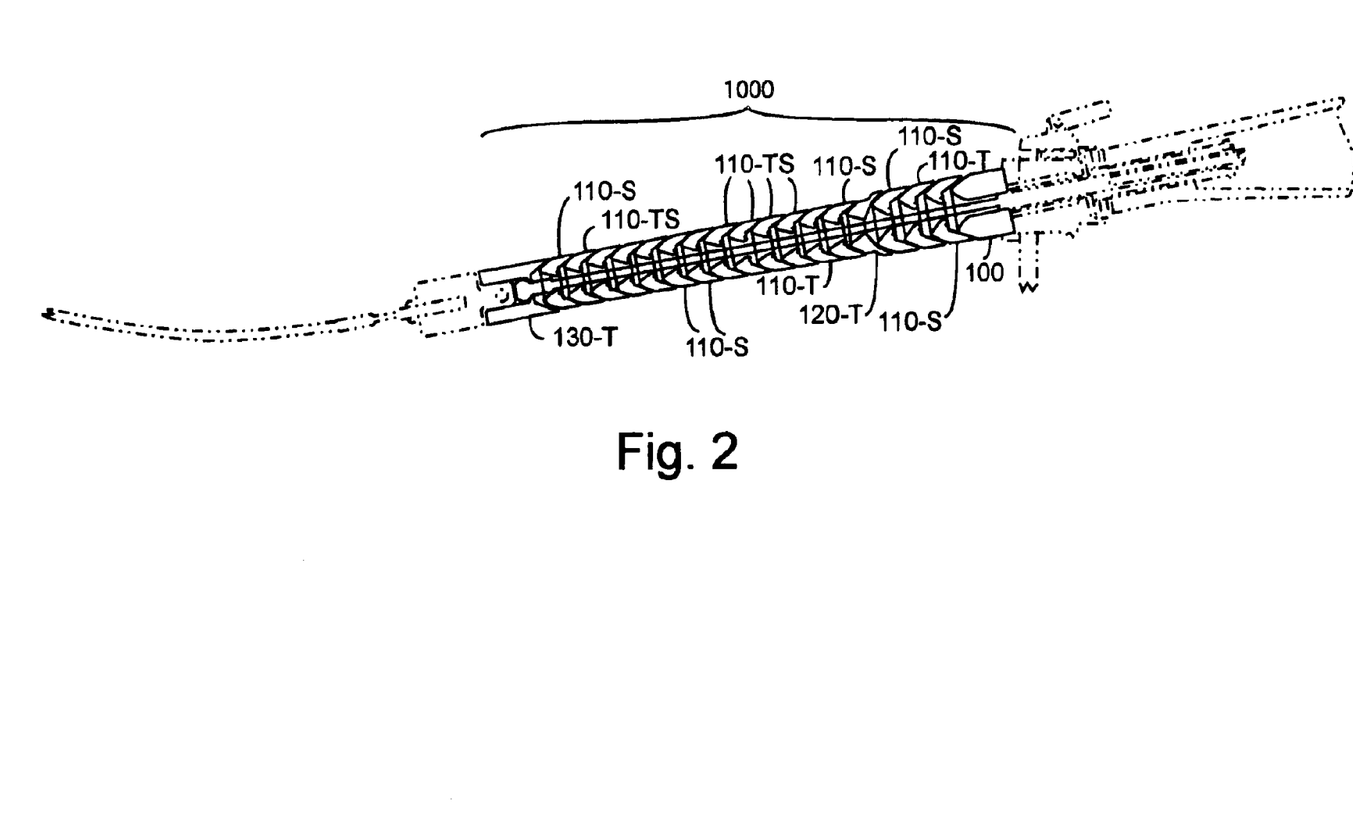
FIG. 2 illustrates a flexible arm including a linkage assembly 1000 in accord with the invention providing increased stiffness when experimentally compared with several alternatives.

FIG. 2 illustrates a flexible arm including a linkage assembly 1000 in accord with the invention providing increased stiffness when experimentally compared with several alternatives.

Figure 3A:
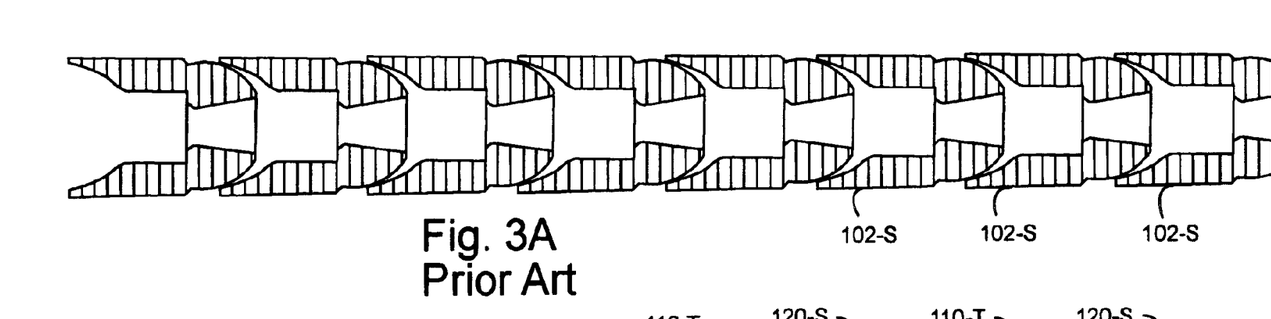
FIG. 3A illustrates a metallic linkage assembly as taught by the prior art.

FIG. 3A illustrates a metallic linkage assembly as taught by the prior art.

Figure 3B:
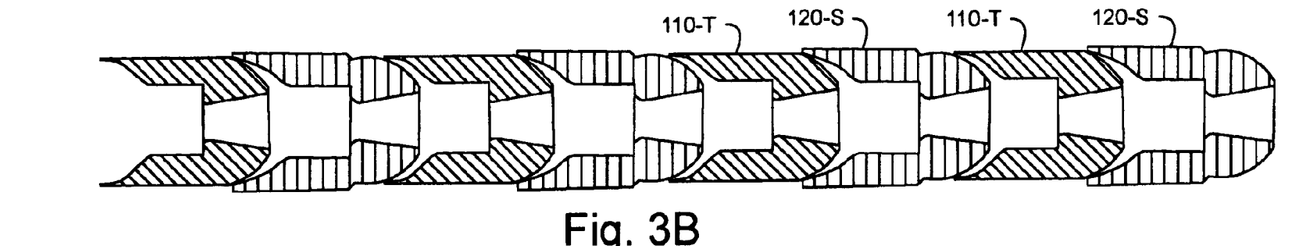
FIG. 3B illustrates a metallic linkage assembly 1000 of FIG. 2.

FIG. 3B illustrates a metallic linkage assembly 1000 of FIG. 2.

Figure 3C:
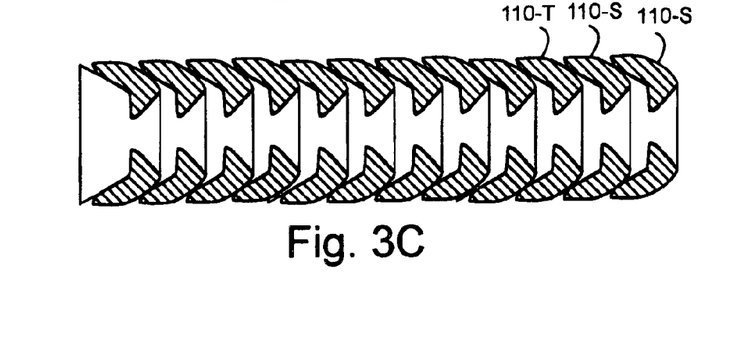
FIG. 3C illustrates a preferred metallic linkage assembly 1000 of FIG. 2.

FIG. 3C illustrates a preferred metallic linkage assembly 1000 of FIG. 2.

In FIG. 2, linkage assembly 1000 includes a link 130-T coupling with link 110-S and link 100 coupling with link 110-S. As used herein a link 110-S will refer to a link shape 110 composed primarily of stainless steel. A link 110-T will refer to a link shape 110 composed primarily of titanium.

A link may employ two or more distinct metallic compounds, typically one for each contact surface. Note that it is also within the scope of the invention to use separate materials within a link for the contact surfaces, as well as for the body joining the two contact surfaces.

A link 110-TS refers to a link possessing a concave surface primarily composed of a titanium alloy, and a convex surface primarily composed of a stainless steel alloy. Note that a link 110-ST refers to a link possessing a concave surface primarily composed of a stainless steel alloy, and a convex surface primarily composed of a titanium alloy. The concave and convex surfaces both support a tensioning cable traversing through their link.

The concave and convex surfaces preferably embody shapes, which for their materials, maximize static friction as well as kinetic friction when contacting each other under tension.

In FIGS. 2, 3B, and 3C, there are four linkage shapes used, 100, 110, 120 and 130. Each linkage shape includes at least one contact surface, which contact couples to a neighboring contact surface of another link. Links 100 and 130 each have exactly one contact surface, which are convex and concave, respectively. Links 110 and 120 each have two contact surfaces, one concave and the other convex.

The invention includes linkage assemblies provided with a tensioning cable and including the following. A first link forming a first contact surface composed of a first contact material. A second link forming a second contact surface composed of a second contact material. The tensioning cable traversing through the first link and the second link.

In certain embodiments, a high friction coupling between the first link and the second link is created by the first contact surface contacting the second contact surface when induced by the tensioning cable. The first contact material is distinct from the second contact material. Each of the contact materials is primarily composed of a respective metallic compound. The first contact surface, composed of the first contact material, contacting the second contact surface, composed of the second contact material, has a higher friction coefficient than results from composing both contact surfaces of either contact materials. This higher friction coefficient is preferably greater than 0.3.

Preferably, each of the respective metallic compounds is primarily composed of at least one alloy containing at least one member of the collection comprising: iron, copper, and titanium. However, other materials including other metals and alloys may be useable.

Further preferred, each of the respective metallic compounds is primarily composed of an alloy belonging to the collection comprising: stainless steel, titanium, and nitinol.

Figure 4:
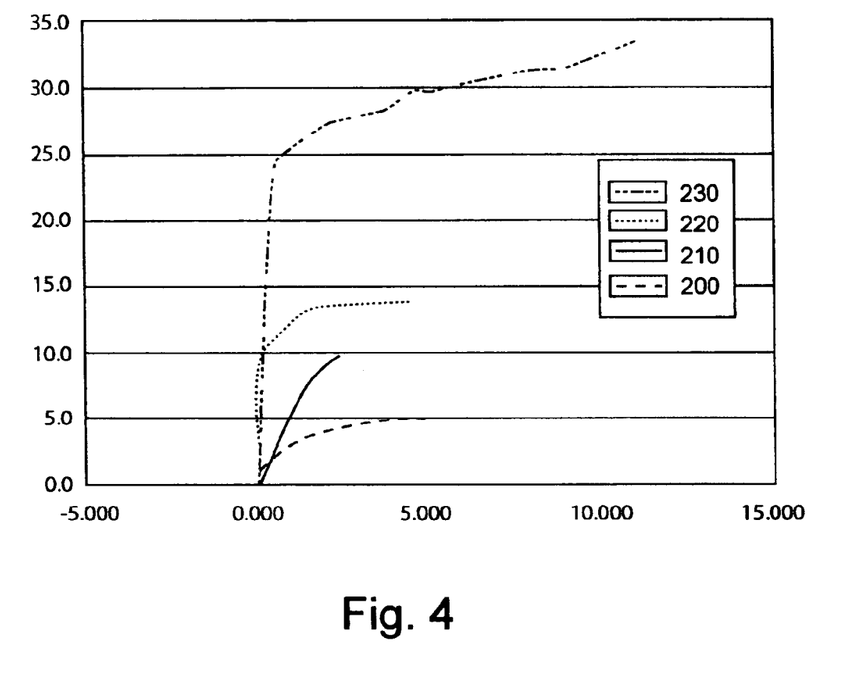
FIG. 4 illustrates experimental results obtained by testing a first link coupling to a second link as illustrated in FIGS. 3A to 3C, each under 200 pound tension.

FIG. 4 illustrates experimental results obtained by testing a first link coupling to a second link as illustrated in FIGS. 3A to 3C, each under 200 pound tension.

Figure 5A:
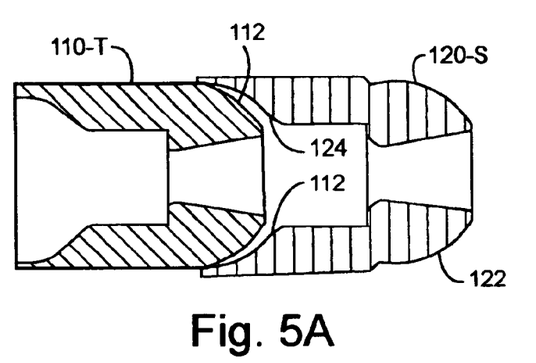
FIGS. 5A and 5B illustrate two links of FIG. 3B coupling with each other through a spherical convex surface contacting a spherical concave surface.
Figure 5B:
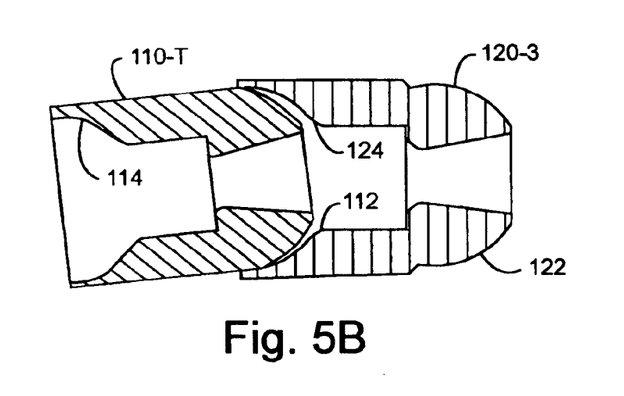

FIGS. 5A and 5B illustrate two links of FIG. 3B coupling with each other through a spherical convex surface contacting a spherical concave surface.

In FIGS. 5A and 5B, the spherical convex surface 112 connects with the semi-spherical concave surface 124. The diameters of the two surfaces are preferably slightly different, with the convex semi-spherical 112 diameter being larger than the semi-spherical diameter of the interfacing concave surface 124. Convex surface 112 and concave surface 124 form an interference fit when the two surfaces contact each other under tension. The wall of link 120-S is sufficiently thin and resilient where the two surfaces come together to provide an area contact between the first link and the second link.

Figure 5C:
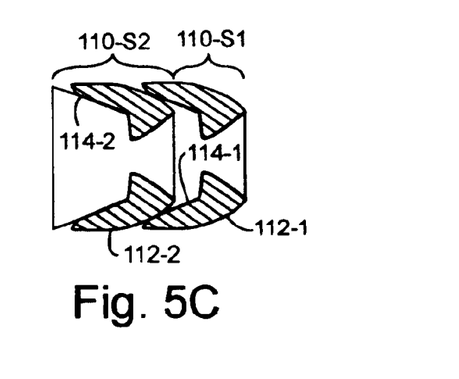
FIG. 5C illustrates two stainless steel links of FIG. 3C coupling with each other through a spherical convex surface contacting a conical concave surface.

FIG. 5C illustrates two stainless steel links of FIG. 3C coupling with each other through a spherical convex surface contacting a conical concave surface.

Figure 5D:
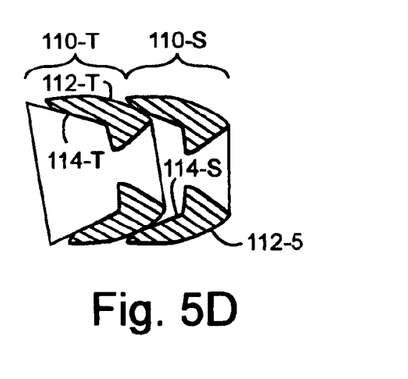
FIG. 5D illustrates two links of FIG. 3C coupling with each other through a spherical convex titanium surface contacting a conical concave stainless steel surface.

FIG. 5D illustrates two links of FIG. 3C coupling with each other through a spherical convex titanium surface contacting a conical concave stainless steel surface.

In FIG. 5C, the spherical convex surface 112-2 connects with the conical concave surface 114-1. The diameters of the two surfaces are preferably slightly different, with the convex semi-spherical 112-2 diameter being larger than the conical diameter of the interfacing concave surface 114-1. Convex surface 112-2 and concave surface 114-1 form an interference fit when the two surfaces contact each other under tension. The wall of link 110-S1 is sufficiently thin and resilient where the two surfaces come together to provide an area of contact with each other. Percentages referenced in this paragraph were percent elongation. Taken from Reference: *Materials Science and Engineering, 3rd Edition*, W. Callister copyright 1985

In FIG. 5D, the spherical convex surface 112-T connects with the conical concave surface 114-S. The diameters of the two surfaces are preferably slightly different, with the convex semi-spherical 112-T diameter being larger than the conical diameter of the interfacing concave surface 114-S. Convex surface 112-T and concave surface 114-S form an interference fit when the two surfaces contact each other under tension. The wall of link 110-S1 is sufficiently thin and resilient where the two surfaces come together to provide an of area contact with each other.

In FIGS. 5A to 5D, the circular edge of the opening of each link is preferably concentric with the center of the imaginary sphere in which the surface lies when the links are fully engaged with each other. The edge is rounded to avoid a sharp edge that could damage the tensioning cable. The rounded edge has a very small radius of curvature to maximize the contact area of the mating convex and concave surfaces. The fact that the edge is rounded instead of sharp has negligible effect on the contact area.

The diameters of the convex and mating concave link surfaces may preferably vary over the length of the linkage assembly. This supports the need for increased strength and/or stiffness at the proximal end of the articulating arm near tension block 18, where the applied mechanical moment is greatest. The applied moment is greatest at the proximal end of the flexible arm because the moment arm to the point of loading is greatest. Often, the flexible arm is oriented at the proximal end in a way that amplifies this effect.

The joints at the proximal end of the arm are preferably larger in diameter. This increases their rotational inertia, or resistance to rotation, in addition to providing greater frictional contact area than smaller distal beads located furthest from tension block 18.

The greatest load-bearing link is usually the most proximal link. This link is sunk into the body of the articulating column providing a mechanical lock, prohibiting rotation of this link.

Distal links which need not provide such a great magnitude of resistance to angular displacement, due to the smaller applied moment, are preferably smaller in diameter to facilitate a lighter, less obtrusive design. This is useful in a surgery, where any protruding object may catch on fabric, tape, etc., distracting the surgical personnel.

Links preferably do not deform more than 0.01% from their relaxed circumference when fully loaded. This small deformation is achieved specifically because of the use of metal materials of the joint elements. A plastic bead would have to be impracticably thick to achieve this constraint.

Generally, the interference fit of the balls and sockets of the link, and more importantly, the significant area of contact between them, together provide the rigidity necessary for tissue stabilization in heart surgery. These features also allow the bracket to be adjusted easily and locked into its rigid condition by the application of a moderate force on the cable.

However, the rigidity of the arm can be substantially improved by improving the friction coefficient between links by differing selected materials between the links. This can be accomplished by fabricating adjacent articulating elements of differing materials, or by using coatings or other modifications to the contacting surfaces.

In the experimental data provided in FIG. 4, the links of FIGS. 3A to 3C, each used essentially one metallic compound.

In FIG. 4, the bottom curve 200 shows the performance of an existing link.

In FIG. 4, the second curve 210 is the performance of first link interface from a competitive device made of plastic.

In FIG. 4, the third curve 220 shows the performance of an improved high friction coupling of metallic contact surfaces in accord with certain aspects of the invention. The tensioning cable induces contact between the first contact surface and the second contact surface providing a maximal static friction combined with a maximal kinetic friction between the first link and the second link through a contact region.

The experimental data present by curve 220, uses a contact region is smaller than a maximal contact region obtained from altering at least one member of the collection comprising the first contact surface and the second contact surface. Such alterations include relatively small changes in the shapes and relative sizes of one or both contact surfaces.

In FIG. 4, the top curve 230 shows the performance of the preferred high friction coupling. The tensioning cable induces contact between the first contact surface and the second contact surface providing a maximal static friction combined with a maximal kinetic friction between the first link and the second link through a contact region as found in curve 220. Additionally, the contact materials are stainless steel and titanium.

The applied moment can be thought of as the amount of torque that the arm can resist before undergoing angular displacement.

The important point on these curves is where a device begins to deviate from vertical, not where it plateaus. For instance, curve 200 for Device 1 begins to move around 2 in-lbs, whereas the Ti—SS links with the preferred contact surfaces begin to mode up around 25 in-lbs.

The inventors analyzed the forces on the contact surfaces of a pair of coupling links. This lead to an insight regarding the parameters governing the static equilibrium conditions. The static equilibrium equations were solved for the maximum moment that could be supported prior to slippage at the interface. The inventors found the influence of the friction was very nonlinear.

The friction coefficient of the contacting metallic surface is preferably greater than 0.3. The friction coefficient of the contacting metallic surface is further preferred greater than 0.35. The friction coefficient of the contacting metallic surface is further preferred greater than 0.375. The friction coefficient of the contacting metallic surface is further preferred greater than 0.3875. An analysis performed by the inventors indicates that a flexible arm with a friction coefficient of 0.4 would be twice as stiff as one with a friction coefficient of 0.3.

The flexibility of an articulating column using the invention allows for an attached retractor to reach all portions of an organ, such as the heart. This is because of the small bend radius that has been made possible by the invention. The flexibility afforded by the small bend radius is possible because of the geometry and rigidity of the joints keeping the same stabilization of the organ as prior art device requiring greater bend radii.

The flexibility of an articulating column using this invention is increased over existing designs due to the conical angle at the convex and concave surfaces of the respective links.

Proximal links have a larger conical angle, afforded by their larger overall size. This increases the range of motion of the column by increasing the range of motion of the proximal links near to tension block 18.

Smaller distal links have smaller conical angles, but also smaller distance from the articulating surface to the center of rotation, creating a uniform range of motion throughout the device.

For all links, the tension cable traverses freely through the links when the links are rotated to the extent of their articulating surfaces. This supports the range of motion being limited by the link design rather than the cable.

The rigidity of the articulating column can be attributed to increased friction resulting from a combination of geometric and materials factors.

The geometry of the two metallic contacting surfaces preferably acts to amplify the contact forces that are produced by applying tension to the tensioning cable.

In the case of certain embodiments of the invention, the spherical convex surface of one link preferably mates with a conical concave surface of another link. This mismatch produces larger contact forces distributed over a smaller relative area. With metals, the magnitude of these contact forces must exceed a threshold for static frictional forces to meet conditions of static equilibrium under a given applied moment. The radius of curvature of the convex surface is preferably large enough such to provide an adequate amount of contact area, further increasing the frictional forces.

A transition link that joins two links of different diameter may have spherical surfaces on both the convex and concave contact surfaces to facilitate the transition within the confined space. These geometric factors compliment the material selection, designed to increase the coefficient of friction between links.

Certain preferred flexible arms are fixed to the body of the clamp 18, and the terminal element, or in some embodiments several terminal elements, may be fixed to a surgical device. In alternate embodiments all joints may be flexible.

Figure 6A:
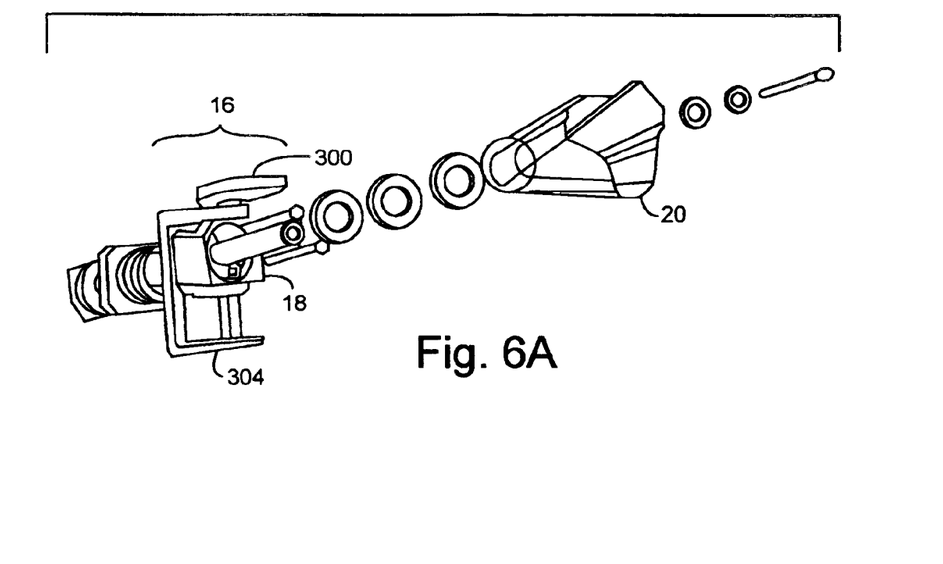
FIG. 6A is an exploded view of item 16 and the rotatable member 20 of FIG. 2.

FIG. 6A is an exploded view of item 16 and the rotatable member 20 of FIG. 2.

In FIG. 6A, the mechanism that supports the articulating column attaches to the supporting structure using a "C" bracket 304 and a tension block 18 applies tension to the supporting structure. This connection mechanism is both secure and is capable of a rapid disconnect.

In FIG. 6A, the tension block 16 is forced down by a screw mechanism that is driven by turning handle 300. The advantage of this pivoted handle is that the screw mechanism does not extend further than 3 mm past the upper surface of the clamp for a profile suitable for less invasive surgery.

Figure 6B:
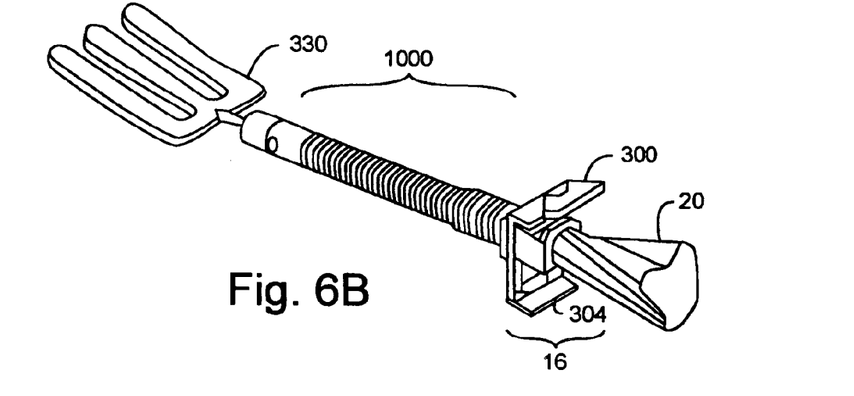
FIG. 6B shows the present invention with an alternate retraction mechanism 330.

FIG. 6B shows the present invention with an alternate retraction mechanism 330.

This and other attachments to an articulating column are possible and those skilled in the art can make suitable modifications for attachment of at least a variety of medical tools. The usefulness of the invention is not limited in scope to medical applications. The scope of the invention is intended to cover any linkage assembly of a flexible arm needing improved rigidity.

Figure 7A:
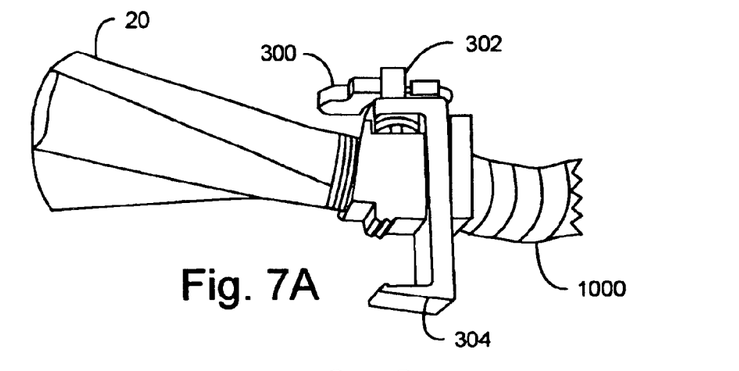
FIG. 7A shows a close-up of the ergonomically designed handle 20 of FIGS. 2 and 6A.

FIG. 7A shows a close-up of the ergonomically designed handle 20 of FIGS. 2 and 6A.

In FIG. 7A, handle 20 has a helical angle suited for right-handed people to oppose the thumb when tightening the handle. Also shown is a better view of clamp apparatus 16. Tension block 18 is driven towards "C" bracket 304 by screw 302 when turning pivot handle 300. This exemplary embodiment is not the only attachment means to support an articulating column including the inventions linkage assembly 1000. Those skilled in the art will appreciate that other attachments are possible and may be considered as alternate embodiments of the present invention.

Figure 7B:
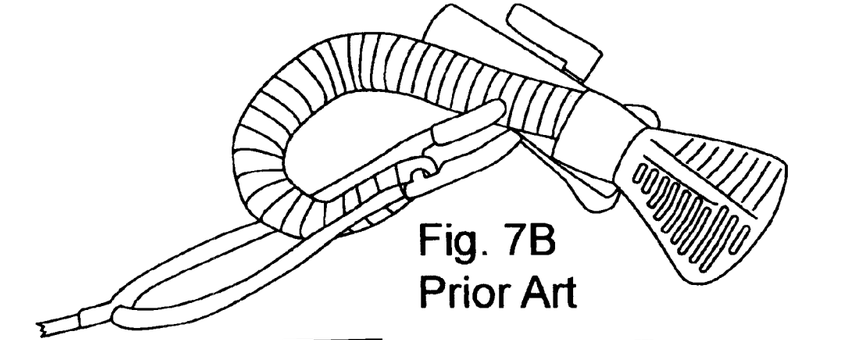
FIGS. 7B, 7C, and 7D, illustrate handles for other commercially available articulating columns.
Figures 7C, 7D:
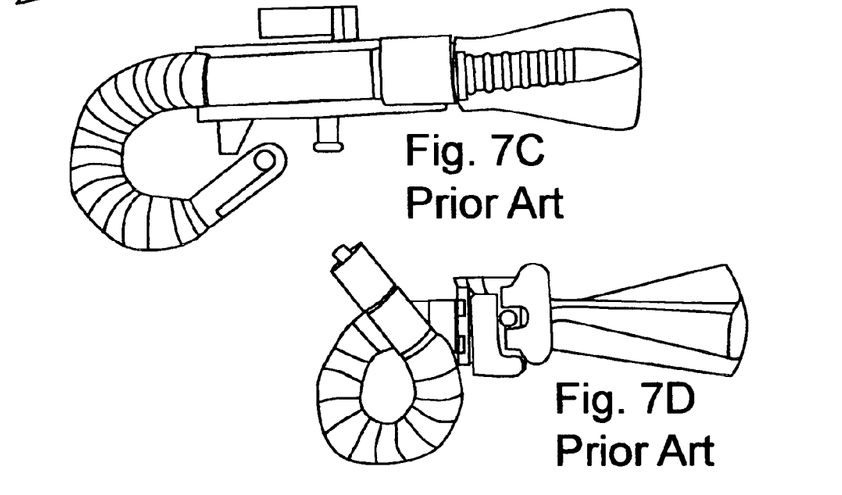

FIGS. 7B, 7C, and 7D, illustrate handles for other commercially available articulating columns.

The present invention allows an articulating column with a greater range of motion or smaller flexible radius of curvature. This can be attributed to the conical angles used in the convex surfaces of each articulating bead, through which the tension cable passes.

In FIG. 7A, the proximal 4 beads have a conical angle of 40 degrees where as the remaining distal beads have a conical angle of 25 degrees. The larger conical angle allows for increased flexibility because the cable has more space to bend.

Although exemplary embodiments of the invention have been described in detail above, many additional modifications are possible without departing materially from the novel teachings and advantages of the invention.

For example, different dissimilar metals may be considered for different friction coefficients, different contact surfaces achieving similar static equilibrium requirements, to create the flexible arm linkage assemblies. The flexible arms may use different support attachment mechanisms and different retractors for connection to the articulating column.

What is claimed is:

1. A flexible arm linkage apparatus provided with a tensioning cable, comprising:

a first link forming a first contact surface composed of a first contact material and approximating a partial convex surface supporting said tensioning cable passing through said first contact surface;

a second link forming a second contact surface composed of a second contact material and approximating a partial concave surface supporting said tensioning cable passing through said second contact surface; and a high friction coupling between said first link and said second link is created by said first contact surface contacting said second contact surface when induced by said tensioning cable;

wherein said first contact material is distinct from said second contact material;

wherein each of said first contact material and said second contact material is primarily composed of a respective metallic compound;

wherein said first contact surface composed of said first contact material contacting said second contact surface composed of said second contact material has a friction coefficient greater than each member of the collection comprising:

a friction coefficient value of 0.3;

said first contact surface composed of said first contact material contacting said second contact surface composed of said first contact material; and said first contact surface composed of said second contact material contacting said second contact surface composed of said second contact material, wherein said first link further forms a third contact surface composed of a third contact material and approximating a second partial concave surface supporting said tensioning cable passing through said third contact surface;

wherein said apparatus is further comprised of a third link forming a fourth contact surface composed of a fourth contact material and approximating a second partial convex surface supporting said tensioning cable passing through said fourth contact surface; and a second high friction coupling between said first link and said third link is created by said third contact surface contacting said fourth contact surface when induced by said tensioning cable;

wherein each of said third and said fourth contact material is primarily composed of a respective metallic compound.

2. The apparatus of claim 1,
wherein each of said respective metallic compounds is primarily composed of at least one alloy containing at least one member of the collection comprising: iron, copper, and titanium.

3. The apparatus of claim 2,
wherein each of said respective metallic compounds is primarily composed of an alloy belonging to the collection comprising: stainless steel, titanium, and nitinol.

4. The apparatus of claim 1,
wherein said first link is composed primarily of said first contact material.

5. The apparatus of claim 4,
wherein said second link is composed primarily of said second contact material.

6. The apparatus of claim 1,
wherein said first contact surface composed of said first contact material contacting said second contact surface composed of said second contact material has said friction coefficient greater than said friction coefficient value of 0.35.

7. The apparatus of claim 6,
wherein said first contact surface composed of said first contact material contacting said second contact surface composed of said second contact material has said friction coefficient greater than said friction coefficient value of 0.375.

8. The apparatus of claim 7,
wherein said first contact surface composed of said first contact material contacting said second contact surface composed of said second contact material has said friction coefficient greater than said friction coefficient value of 0.3875.

9. The apparatus of claim 1,
wherein said second link is composed primarily of said second contact material.

10. The apparatus of claim 1,
wherein said first contact surface contacting said second contact surface when induced by said tensioning cable further provides a maximal static friction combined with a maximal kinetic friction between said first link and said second link.

11. The apparatus of claim 1,
wherein said third contact material is distinct from said fourth contact material;

wherein said third contact surface composed of said third contact material contacting said fourth contact surface composed of said fourth contact material has a higher friction coefficient than each member of the collection comprising:

said third contact surface composed of said third contact material contacting said fourth contact surface composed of said third contact material; and said third contact surface composed of said fourth contact material contacting said fourth contact surface composed of said fourth contact material.

12. The apparatus of claim 1,
wherein said third contact material is essentially said first contact material.

13. The apparatus of claim 12,
wherein said fourth contact material is essentially said second contact material.

14. The apparatus of claim 1,
wherein said partial concave surface is distinct from said second partial concave surface.

15. The apparatus of claim 1,
wherein said first contact surface essentially borders said third contact surface.

16. The apparatus of claim 1,
wherein said first link includes said first contact surface coupled to said third contact surface by a hollow rod supporting said tensioning cable traversing through said first contact surface and through said third contact surface.

17. A method of making a flexible arm linkage assembly with a tensioning cable, comprising the steps of:

providing a first link forming a first contact surface composed of a first contact material and approximating a partial convex surface supporting said tensioning cable passing through said first contact surface;

providing a second link forming a second contact surface composed of a second contact material and approximating a partial concave surface supporting said tensioning cable passing through said second contact surface; and said tensioning cable inducing a contact between said first contact surface and said second contact surface to create a high friction coupling between said first link and said second link;

wherein said first contact material is distinct from said second contact material;

wherein each of said first contact material and said second contact material is primarily composed of a respective metallic compound;

wherein said first contact surface composed of said first contact material contacting said second contact surface composed of said second contact material has a friction coefficient greater than each member of the collection comprising:

a friction coefficient value of 0.3;

said first contact surface composed of said first contact material contacting said second contact surface composed of said first contact material; and said first contact surface composed of said second contact material contacting said second contact surface composed of said second contact material, wherein said first link further forms a third contact surface composed of a third contact material;

wherein said method is further comprised of the steps of:

providing a third link forming a fourth contact surface composed of a fourth contact material and approximating a second partial convex surface supporting said tensioning cable passing through said fourth contact surface; and said tensioning cable inducing a second high friction coupling between said first link and said third link by said third contact surface contacting said fourth contact surface when induced by said tensioning cable;

wherein each of said third contact material and said fourth contact material is primarily composed of a respective metallic compound.

18. The method of claim 17, wherein each of said respective metallic compounds is primarily composed of at least one alloy containing at least one member of the collection comprising: iron, copper, and titanium.

19. The method of claim 18, wherein each of said respective metallic compounds is primarily composed of an alloy belonging to the collection comprising: stainless steel, titanium, and nitinol.

20. The method of claim 17, wherein said first link is composed primarily of said first contact material.

21. The method of claim 20, wherein said second link is composed primarily of said second contact material.

22. The method of claim 17, wherein said first contact surface composed of said first contact material contacting said second contact surface composed of said second contact material has said friction coefficient greater than said friction coefficient value of 0.35.

23. The method of claim 22, wherein said first contact surface composed of said first contact material contacting said second contact surface composed of said second contact material has said friction coefficient greater than said friction coefficient value of 0.375.

24. The method of claim 23, wherein said first contact surface composed of said first contact material contacting said second contact surface composed of said second contact material has said friction coefficient greater than said friction coefficient value of 0.3875.

25. The method of claim 17, wherein said second link is composed primarily of said second contact material.

26. The method of claim 17, wherein the step of said tensioning cable inducing contact between said first contact surface and said second contact surface is further comprised of the steps of said tensioning cable inducing contact between said first contact surface and said second contact surface providing a maximal static friction combined with a maximal kinetic friction between said first link and said second link.

27. The method of claim 17, wherein said third contact material is distinct from said fourth contact material;

wherein said third contact surface composed of said third contact material contacting said fourth contact surface composed of said fourth contact material has a higher friction coefficient than each member of the collection comprising:

said third contact surface composed of said third contact material contacting said fourth contact surface composed of said third contact material; and said third contact surface composed of said fourth contact material contacting said fourth contact surface composed of said fourth contact material.

28. The method of claim 17, wherein said third contact material is essentially said first contact material.

29. The method of claim 28, wherein said fourth contact material is essentially said second contact material.

30. The method of claim 17, wherein said partial concave surface is distinct from said second partial concave surface.

31. The method of claim 17, wherein said partial convex surface is distinct from said second partial convex surface.

32. The method of claim 17, wherein said partial convex surface further approximates a hemisphere supporting said tensioning cable passing through said first contact surface.

33. The method of claim 17, wherein said partial concave surface further approximates a partial cone supporting said tensioning cable passing through said second contact surface.

34. Said flexible arm linkage assembly as a product of the method of claim 17.

35. A method of making a flexible arm, comprising the steps of claim 17, providing a flexible arm linkage assembly.

36. Said flexible arm as a product of the process of claim 35.

37. A flexible arm linkage apparatus provided with a tensioning cable, comprising:

a first link forming a first contact surface composed of a first contact material and approximating a first partial convex surface supporting said tensioning cable passing through said first contact surface;

a second link forming a second contact surface composed of a second contact material and approximating a first partial concave surface supporting said tensioning cable passing through said second contact surface; and a high friction coupling between said first link and said second link is created by said first contact surface contacting said second contact surface when induced by said tensioning cable;

wherein each of said first contact material and said second contact material is primarily composed of a respective metallic compound;

wherein said first contact surface contacting said second contact surface when induced by said tensioning cable further provides a maximal static friction combined with a maximal kinetic friction between said first link and said second link through a contact region;

wherein said contact region is smaller than a maximal contact region obtained from altering at least one member of the collection comprising said first contact surface and said second contact surface; and wherein said first contact surface composed of said first contact material contacting said second contact surface composed of said second contact material has a friction coefficient greater than a friction coefficient value of 0.3, wherein said first link further forms a third contact surface composed of a third contact material and approximating a second partial concave surface supporting said tensioning cable passing through said third contact surface;

wherein said apparatus is further comprised of
a third link forming a fourth contact surface composed of a fourth contact material and approximating a second partial convex surface supporting said tensioning cable passing through said fourth contact surface; and
a second high friction coupling between said first link and said third link is created by said third contact surface contacting said fourth contact surface when induced by said tensioning cable;
wherein each of said third and said fourth contact material is primarily composed of a respective metallic compound.

38. The apparatus of claim 37,
wherein each of said respective metallic compounds is primarily composed of at least one alloy containing at least one member of the collection comprising: iron, copper, and titanium.

39. The apparatus of claim 38,
wherein each of said respective metallic compounds is primarily composed of an alloy belonging to the collection comprising: stainless steel, titanium, and nitinol.

40. The apparatus of claim 37,
wherein said first link is composed primarily of said first contact material.

41. The apparatus of claim 40,
wherein said second link is composed primarily of said second contact material.

42. The apparatus of claim 37,
wherein said first contact surface composed of said first contact material contacting said second contact surface composed of said second contact material has said friction coefficient greater than said friction coefficient value of 0.35.

43. The apparatus of claim 42,
wherein said first contact surface composed of said first contact material contacting said second contact surface composed of said second contact material has said friction coefficient greater than said friction coefficient value of 0.375.

44. The apparatus of claim 43,
wherein said first contact surface composed of said first contact material contacting said second contact surface composed of said second contact material has said friction coefficient greater than said friction coefficient value of 0.3875.

45. The apparatus of claim 37,
wherein said second link is composed primarily of said second contact material.

46. The apparatus of claim 37,
wherein said third contact surface contacting said fourth contact surface when induced by said tensioning cable further provides a second maximal static friction combined with a second maximal kinetic friction between said first link and said third link through a second contact region; and
wherein said second contact region is smaller than a second maximal contact region obtained from altering at least one member of the collection comprising said third contact surface and said fourth contact surface.

47. The apparatus of claim 46,
wherein said third contact material is essentially said first contact material.

48. The apparatus of claim 47,
wherein said fourth contact material is essentially said second contact material.

49. The apparatus of claim 46,
wherein said partial convex surface is distinct from said second partial convex surface.

50. The apparatus of claim 37,
wherein said first partial concave surface is distinct from said second partial concave surface.

51. The apparatus of claim 37,
wherein said first contact surface essentially borders said third contact surface.

52. The apparatus of claim 37,
wherein said first link includes said first contact surface coupled to said third contact surface by a hollow rod supporting said tensioning cable traversing through said first contact surface and through said third contact surface.

53. The apparatus of claim 37,
wherein said first contact material is distinct from said second contact material.

54. The apparatus of claim 53,
wherein said first contact surface composed of said first contact material contacting said second contact surface composed of said second contact material has a higher friction coefficient than each member of the collection comprising:
said first contact surface composed of said first contact material contacting said second contact surface composed of said first contact material; and
said first contact surface composed of said second contact material contacting said second contact surface composed of said second contact material.

55. The apparatus of claim 37,
wherein said partial convex surface further approximates a hemisphere supporting said tensioning cable passing through said first contact surface.

56. The apparatus of claim 37,
wherein said partial concave surface further approximates a partial cone supporting said tensioning cable passing through said second contact surface.

57. A method of making a flexible arm linkage assembly provided with a tensioning cable, comprising the steps of:
providing a first link forming a first contact surface composed of a first contact material and approximating a first partial convex surface supporting said tensioning cable passing through said first contact surface;
providing a second link forming a second contact surface composed of a second contact material and approximating a first partial concave surface supporting said tensioning cable passing through said second contact surface; and
said tensioning cable inducing a high friction coupling between said first link and said second link by said first contact surface contacting said second contact surface;
wherein the step of said tensioning cable inducing said high friction coupling is further comprised of the step:
said first contact surface contacting said second contact surface when induced by said tensioning cable providing a maximal static friction combined with a maximal kinetic friction between said first link and said second link through a contact region;
wherein each of said first contact material and said second contact material is primarily composed of a respective metallic compound;
wherein said contact region is smaller than a maximal contact region obtained from altering at least one member of the collection comprising said first contact surface and said second contact surface; and wherein said first contact surface composed of said first contact material contacting said second contact surface composed of said second contact material has a friction coefficient greater than a friction coefficient value of 0.3, wherein said first link further forms a third contact surface composed of a third contact material and approximating a second partial concave surface supporting said tensioning cable passing through said third contact surface;

wherein said method is further comprised of the steps of:

providing a third link forming a fourth contact surface composed of a fourth contact material and approximating a second partial convex surface supporting said tensioning cable passing through said fourth contact surface; and said tensioning cable inducing a second high friction coupling between said first link and said third link by said third contact surface contacting said fourth contact surface;

wherein each of said third and said fourth contact material is primarily composed of a respective metallic compound.

58. The method of claim 57, wherein each of said respective metallic compounds is primarily composed of at least one alloy containing at least one member of the collection comprising: iron, copper, and titanium.

59. The method of claim 58, wherein each of said respective metallic compounds is primarily composed of an alloy belonging to the collection comprising: stainless steel, titanium, and nitinol.

60. The method of claim 57, wherein said first link is composed primarily of said first contact material.

61. The method of claim 60, wherein said second link is composed primarily of said second contact material.

62. The method of claim 57, wherein said first contact surface composed of said first contact material contacting said second contact surface composed of said second contact material has said friction coefficient greater than said friction coefficient value of 0.35.

63. The method of claim 62, wherein said first contact surface composed of said first contact material contacting said second contact surface composed of said second contact material has said friction coefficient greater than said friction coefficient value of 0.375.

64. The method of claim 63, wherein said first contact surface composed of said first contact material contacting said second contact surface composed of said second contact material has said friction coefficient greater than said friction coefficient value of 0.3875.

65. The method of claim 57, wherein said second link is composed primarily of said second contact material.

66. The method of claim 57, wherein the step of said tensioning cable inducing said second high friction coupling is further comprised of the step:

said third contact surface contacting said fourth contact surface when induced by said tensioning cable providing a second maximal static friction combined with a second maximal kinetic friction between said first link and said third link through a second contact region; and wherein said second contact region is smaller than a second maximal contact region obtained from altering at least one member of the collection comprising said third contact surface and said fourth contact surface.

67. The method of claim 66, wherein said third contact material is essentially said first contact material.

68. The method of claim 67, wherein said fourth contact material is essentially said second contact material.

69. The method of claim 57, wherein said first partial concave surface is distinct from said second partial concave surface.

70. The method of claim 57, wherein said first contact surface essentially borders said third contact surface.

71. The method of claim 57, wherein said first link includes said first contact surface coupled to said third contact surface by a hollow rod supporting said tensioning cable traversing through said first contact surface and through said third contact surface.

72. The method of claim 57, wherein said first partial convex surface is distinct from said second partial convex surface.

73. The method of claim 57, wherein said first contact material is distinct from said second contact material.

74. The method of claim 73, wherein said first contact surface composed of said first contact material contacting said second contact surface composed of said second contact material has a higher friction coefficient than each member of the collection comprising:

said first contact surface composed of said first contact material contacting said second contact surface composed of said first contact material; and said first contact surface composed of said second contact material contacting said second contact surface composed of said second contact material.

75. The method of claim 57, wherein said partial convex surface further approximates a hemisphere supporting said tensioning cable passing through said first contact surface.

76. The method of claim 57, wherein said first partial concave surface further approximates a partial cone supporting said tensioning cable passing through said second contact surface.

77. Said flexible arm linkage assembly as a product of the method of claim 57.

78. A method of making a flexible arm, comprising the steps of claim 57 providing a flexible arm linkage assembly.

79. Said flexible arm as a product of the process of claim 78.

* * * * *